United States Patent [19]

Mewshaw et al.

[11] Patent Number: 5,530,157
[45] Date of Patent: Jun. 25, 1996

[54] ANTI-INFLAMMATORY BENZOIC ACID DERIVATIVES

[75] Inventors: Richard Mewshaw, Princeton, N.J.; Gregory S. Hamilton, Cantonsville, Md.

[73] Assignee: Scios Nova Inc., Mountain View, Calif.

[21] Appl. No.: 389,662

[22] Filed: Feb. 16, 1995

[51] Int. Cl.$^6$ ............................. C07C 63/36; C07C 65/00
[52] U.S. Cl. .................. 562/490; 562/491; 562/432; 562/473; 562/441; 562/454; 562/468; 562/474
[58] Field of Search ........................... 562/473, 490, 562/491, 432, 441, 454, 468, 474; 514/567, 568

[56] References Cited

FOREIGN PATENT DOCUMENTS

| 1328279 | 9/1988 | Canada. |
| 0514264 | 11/1992 | European Pat. Off.. |
| 96234 | 5/1972 | France. |
| 62-103057 | 5/1987 | Japan. |
| 229822 | 9/1990 | Japan. |
| 229136 | 9/1990 | Japan. |
| 339204 | 12/1993 | Japan. |

OTHER PUBLICATIONS

Garratt et al., "Wittig Reactions of 1,2-Dihydro-1,2-bis-(triphenylphosphoranylidene)-benzocyclobutene-1, 2-quinone. The Synthesis of Dibenzo[a,c]benzo[3,4]cyclobuta[1,2-f]cyclo-octane" *J. Chem. Soc.* (1970) 2137-2141.
Nogradi, M., "The Synthesis of Some Dibenzo[a,d]-cycloheptenes, Tribenzo[a,c,e]cycloheptenes and Heterocyclic Analogues, Model Compounds for Conformational Studies" *Acta Chimica Academiae Scientarum Hungaricae* (1978) 96:393–404.
Burch et al., "N-(Fluorenyl-9-methoxycarbonyl)amino acids, a class of antiinflammatory agents with a different mechanism of action" *Proc. Natl. Acad. Sci. USA* (1991) 88:335–359.

*Primary Examiner*—Paul J. Killos
*Attorney, Agent, or Firm*—Peter R. Shearer; Marjorie L. Jarvis

[57] ABSTRACT

Novel benzoic acid derivatives have the formula:

<chemical structure: benzene ring with R$^1$, R$^2$ substituents and Y-R group, connected via X to another benzene ring bearing COOH> wherein

—X— represents $C_1$ to $C_6$ alkylene, $C_2$ to $C_6$ alkenylene or a divalent moiety having the structure —(CH$_2$)$_m$—Z— in which m is an integer from 0 to 3 and Z represents —O—, —S— or —NH—;

—Y— represents a direct bond, C1 to $C_6$ alkylene, $C_2$ to $C_6$ alkenylene or a divalent moiety having the structure —(CH$_2$)$_m$—Z—(CH$_2$)$_n$ in which m and n are each, independently, an integer from 0 to 3 and —Z— represents —O—, —S— or —NH—;

R represents a 5- or 6-membered carbocyclic or heterocyclic ring or a carbocyclic or heterocyclic fused ring system containing up to 10 members in the ring, which carbocyclic, heterocyclic or fused ring system may be saturated or unsaturated and may contain up to two substituents selected from lower alkyl, methoxy, halo and trifluoromethyl; and R$^1$ and R$^2$ are each, independently, selected from hydrogen, lower alkyl, methoxy, halo and trifluoromethyl.

The benzoic acid derivates are useful as anti-inflammatory agents.

24 Claims, No Drawings

ANTI-INFLAMMATORY BENZOIC ACID DERIVATIVES

BACKGROUND OF THE INVENTION

1. Field of the Invention

This invention relates to novel benzoic acid derivative compounds, and more particularly to novel benzoic acid derivatives and pharmaceutical compositions suitable for use as anti-inflammatory agents.

2. Description of the Prior Art

The treatment of inflammatory conditions, such as atopic dermatitis, contact dermatitis, psoriasis, rheumatoid arthritis, glomerulonephritis, osteoarthritis, lupus erythematosus, scleroderma, asthma and irritable bowel disease has in the past involved the use of agents such as aspirin-like nonsteroidal anti-inflammatory agents, glucocorticoids, methotrexate and cyclophosphamide. Unfortunately, these agents generally produce unwanted side effects.

Nonsteroidal anti-inflammatory drugs (NSADs), while reducing inflammatory symptoms, do not prevent progression of disease and have serious side effects, including gastric ulceration. Glucocorticosteroids provide dramatic relief in some diseases but with systemic side effects which often preclude chronic use at efficacious doses. Furthermore, certain cytotoxic agents can provide substantial relief, but elicit major toxicity. Methotrexate has been associated with patient death. Cyclophosphamide has carcinogenic liability. Thus, new agents for treating inflammatory conditions that are free of these adverse side effects are needed.

Burch et al. in "N-(Fluorenyl-9-methoxycarbonyl)amino acids, a class of anti-inflammatory agents with a different mechanism of action", *Proc. Natl. Acad. Sci, USA*, (1991) 88:355–359, discloses several members of a series of (N-fluorenyl-9-methoxycarbonyl)amino acids as possessing a broad spectrum of anti-inflammatory activity. The compounds are disclosed as being active against oxazolone dermatitis in mice and adjuvant arthritis in rat models in which activated T-lymphocytes are implicated. Burch et al. found that the compounds also inhibited T-lympocyte activation in vitro, assessed by using the mixed lymphocyte reaction and that the compounds inhibited the reversed passive Arthus reaction in rats and arachidonic acid-induced dermatitis in mice models in which leukocyte infiltration is responsible for the inflammatory reaction.

SUMMARY OF THE INVENTION

The present invention provides benzoic acid derivatives which are useful as anti-inflammatory agents. In particular, the benzoic acid derivatives of the invention are represented by Formula I

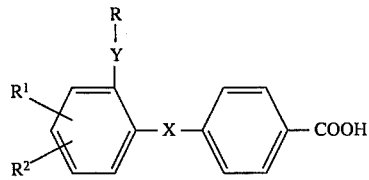

wherein

—X— represents $C_1$ to $C_6$ alkylene, $C_2$ to $C_6$ alkenylene or a divalent moiety having the structure —$(CH_2)_m$—Z— in which m is an integer from 0 to 3 and Z represents —O—, —S— or —NH—;

—Y— represents a direct bond, $C_1$ to $C_6$ alkylene, $C_2$ to $C_6$ alkenylene or a divalent moiety having the structure —$(CH_2)_m$—Z—$(CH_2)_n$— in which m and n are each, independently, an integer from 0 to 3 and —Z— represents —O—, —S— or —NH—;

R represents a monovalent 5- or 6-membered carbocyclic or heterocyclic ring or a carbocyclic or heterocyclic fused ring system containing up to 10 members in the ring, which carbocyclic, heterocyclic or fused ring system may be saturated or unsaturated and may contain up to two substituents selected from lower alkyl, methoxy, halo and trifluoromethyl; and $R^1$ and $R^2$ are each, independently, selected from hydrogen, lower alkyl, methoxy, halo and trifluoromethyl.

Another aspect of the invention includes a method of treating an inflammatory condition which comprises administering to a subject in need of such treatment an anti-inflammatory amount of a compound of Formula I or a pharmaceutically acceptable salt thereof.

Another aspect of the invention includes a pharmaceutical formulation comprising an anti-inflammatory amount of a compound of Formula I or a pharmaceutically acceptable salt thereof and a pharmaceutically acceptable carrier vehicle. Such a composition may be administered in many ways, including topically, rectally, parenterally and orally.

DETAILED DESCRIFFION OF THE INVENTION

Preferred Benzoic Acid Derivative Compounds

As used in the definition of the benzoic acid derivative of Formula I herein, the term "alkylene" refers to a divalent, saturated hydrocarbon chain, which may be straight or branched. The term "alkenylene" refers to a divalent hydrocarbon chain, which may be straight or branched and which contains at least one double bond. The term "lower alkyl" refers to a straight or branched chain alkyl having up to six carbon atoms.

Preferred —X— groups in Formula I are $C_1$ to $C_6$ alkylene and $C_2$ to $C_6$ alkenylene. The most preferred —X— groups are ethylene, i.e. —$CH_2$—$CH_2$—, and ethenylene, i.e. —CH=CH—. When the compound contains olefinic unsaturation in the —X— group, it may be in the trans or the cis conformation or may consist of a mixture of both forms.

In Formula I, —Y— is preferably a direct bond, —O—, —S—, —NH— or the group —$CH_2$—O—, which may be oriented such that the oxygen moiety is bonded either to the group R or to the phenyl ring in Formula I. Most preferably, —Y— is a direct bond.

Preferred R groups are phenyl, which may be mono- or di-substituted at the meta and/or para positions, with the preferred substituents being chloro, methyl or trifluoromethyl, and naphthyl.

Other useful R groups include:

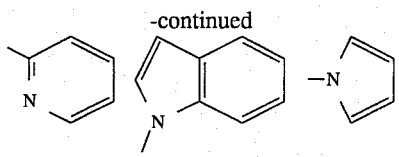

Particularly preferred benzoic acid derivatives of the invention are the following:

4-[2-(2-biphenyl)-E-ethenyl]benzoic acid

4-[2-(2-biphenyl)ethyl]benzoic acid

4-{2-[2-(2-naphthyl)phenyl]-(E)-ethenyl}benzoic acid

4-{2-[2-(3,4-dichlorophenyl)phenyl]-(E)-ethenyl}benzoic acid

2'-phenoxy-4-stilbenecarboxylic acid

Preparation of Benzoic Acid Derivatives

Compounds of this invention are prepared by a variety of synthetic sequences that utilize established chemical transformations. For those compounds in which the bridging group between the benzoic acid group and the phenyl moiety is composed entirely of carbon units, several different routes may be advantageously employed. As shown by the examples, these methods may be used to prepare compounds in which either R is aromatic or heteroaromatic, and in which R is joined to the phenyl moiety directly or with various spacer groups. As illustrated in Scheme I, and exemplified in Example 1, Wittig condensation (G. Wittig and U. Schollkopf, *Berichte* (1954) 87:1318) of an appropriate carboxaldehyde, for example 2-biphenylcarboxaldehyde, with a requisite phosphonate derivative, for example methyl 4-(diethylphosphonomethyl) benzoate, prepared from methyl 4-bromomethylbenzoate and triethylphosphite, provides an ester precursor to inventive compounds containing an olefinic bridging group. Hydrolysis of the ester gives the corresponding benzoic acid derivative. Hydrogenation of the olefin affords the related saturated carbon bridged compound of the invention.

In cases in which the requisite carboxylic acid is available, the aldehyde may be prepared as shown in Scheme I. In other cases, the required aldehydes are conveniently obtained by various well established procedures such as reaction of aryllithium species with dimethylformamide. Examples of these procedures are shown in Schemes II and III. Preparation of certain aldehydes required individual pathways, such as those shown in Schemes IV and V.

Scheme I

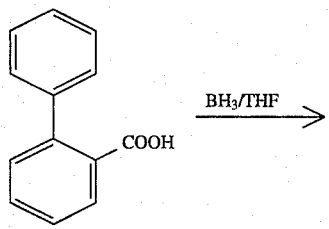

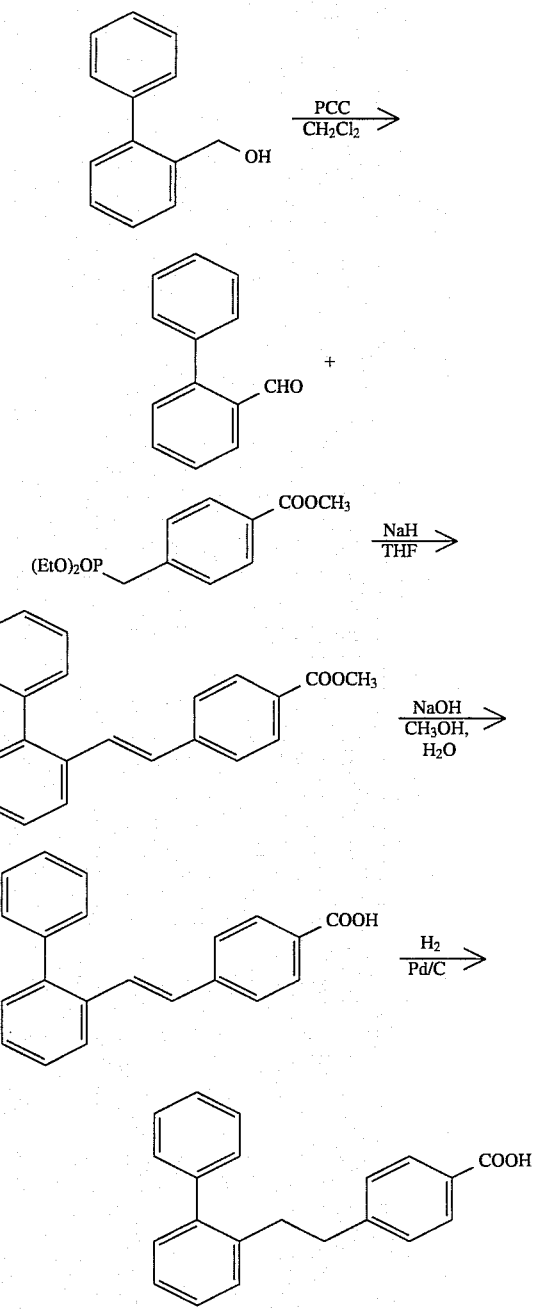

Scheme II
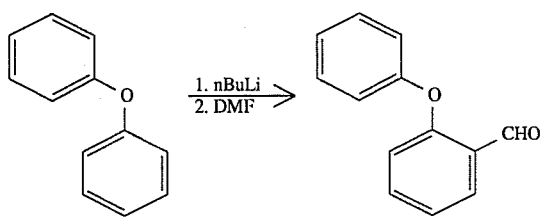
Scheme III
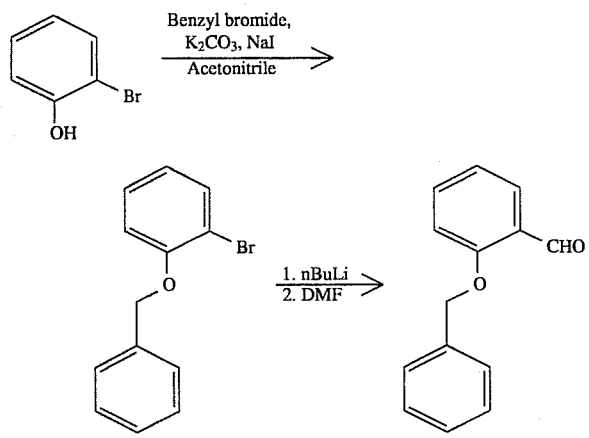
Scheme IV
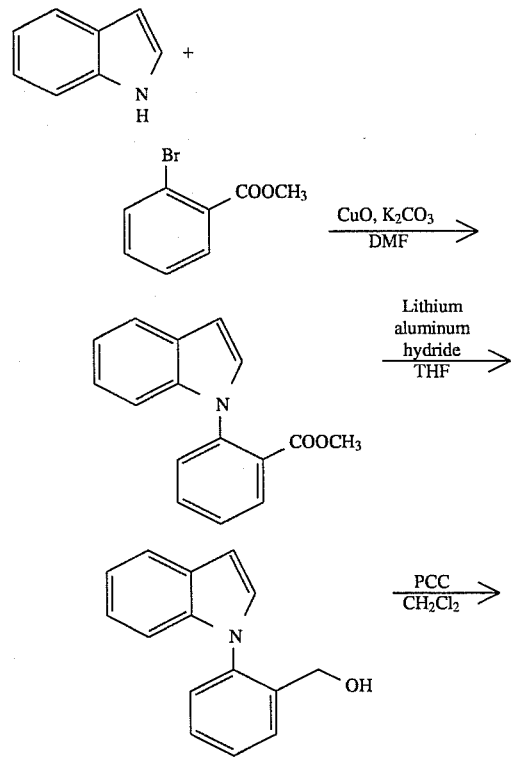
Scheme IV -continued
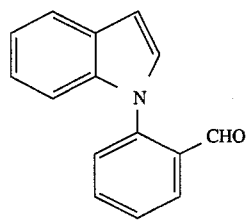
Scheme V
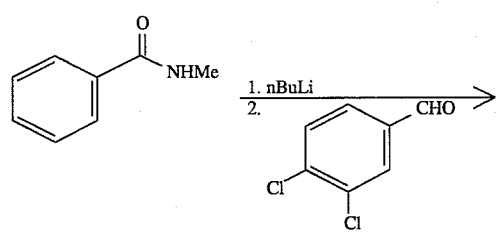
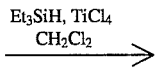
Other compounds of this invention in which a two-carbon chain (saturated or unsaturated) is present in the benzoic acid-to-phenyl bridge and the R group is varied are prepared by palladium-catalyzed coupling of an aryl bromide with an aryl trialkylstannyl derivative (prepared by conversion of the corresponding aromatic bromide to the aryllithium species followed by reaction with trialkyltin chloride), as exemplified in Example 3. For example, as outlined in Scheme VI, 1-(2-bromophenyl)-2-(4-carbomethoxyphenyl)ethylene [prepared by Wittig condensation of 2-bromobenzaldehyde with methyl 4-(diethylphosphonomethyl)benzoate by the general procedure shown in Scheme I] with 2-(tributylstannyl)thiophene [prepared by treatment of 2-lithiothiophene, obtained from n-butyllithium and 2-bromothiophene, with tributyltin chloride) gives an olefinic ester hydrolysis provides a compound of the invention in which R is a 2-thiophenyl substituent.

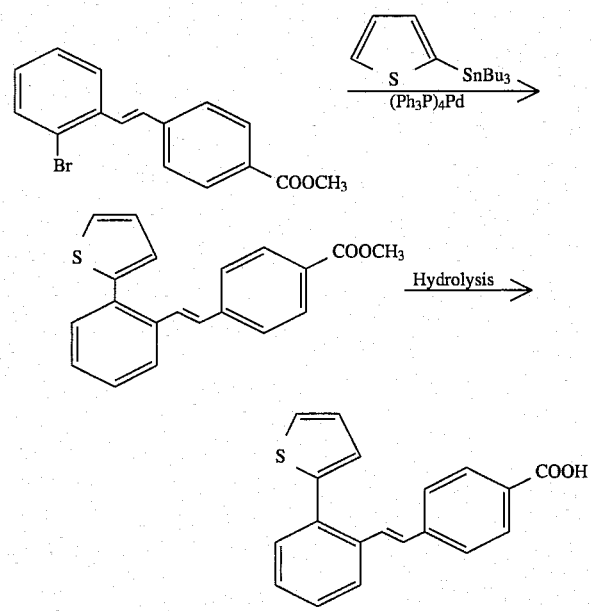

Compounds of the invention in which the —Z— moiety in the benzoic acid-to-phenyl bridge is oxygen are conveniently prepared by Mitsunobu reaction (O. Mitsunobo and M. Yamada, *Bull. Chem. Soc. Jpn.* (1967) 40:2380) between an appropriate alcohol and phenol, for example, methyl 4-hydroxybenzoate, followed by hydrolysis of the ester product. For example, as outlined in Scheme VII, reaction of (2-benzoxy)-3-phenylprop-1-ol with methyl 4-hydroxybenzoate gives methyl 4-[3-(2-benzoxyphenyl)propoxy]benzoate, which is subsequently hydrolyzed to the benzoic acid derivative.

Alcohol derivatives required for the Mitsunobu reactions are obtained by several different routes. A particularly advantageous source of these compounds, as outlined in Scheme VII, involves palladium catalyzed (Heck reaction, *Heck Acc. Chem. Res.* (1979) 12:146) reaction of an aryl halide with an activated olefin, for example, methyl acrylate or methyl 2,4-pentadienoate, to give an aryl substituted olefinic ester which upon sequential hydrogenation and lithium aluminum hydride reduction provides the alcohol required for preparation of inventive compounds in which the —Z— moiety is oxygen. In other cases, alcohols may be obtained via borane reduction of the appropriate carboxylic acid, as described earlier.

Compounds in which the —X— moiety is longer than two carbons, but does not contain oxygen, may be prepared as shown in Scheme VIII. Wittig chemistry is used to homologate the appropriate aryl aldehyde by two carbon units; the ester group is then reduced to the alcohol and subsequently oxidized to the aldehyde, which undergoes a Wittig reaction with the previously described reagent methyl 4-(diethylphosphonomethyl) benzoate.

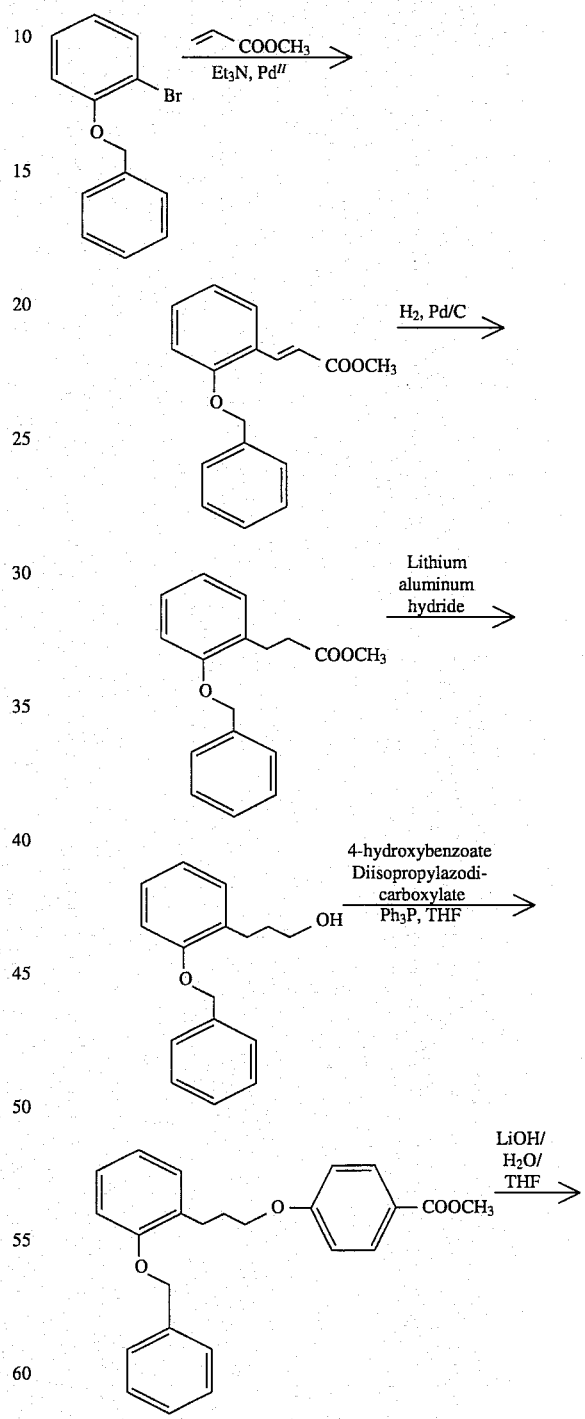

-continued
Scheme VII

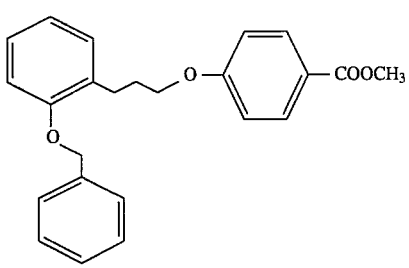

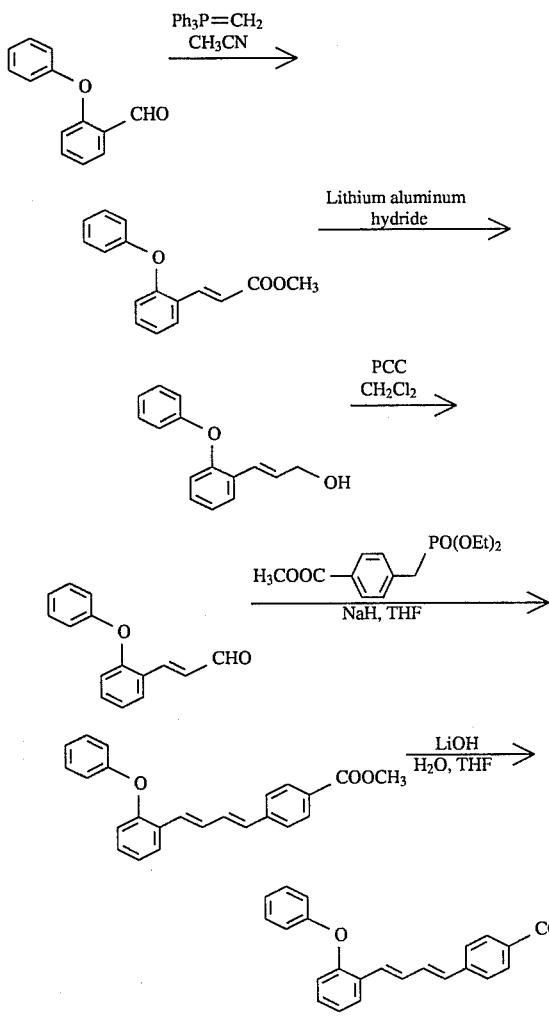

Pharmaceutical Compositions of the Invention

The compounds of the invention are useful for treating a subject, e.g. a human or other mammal, suffering from an inflammatory condition. Conditions which may be treated include, but are not limited to, atopic or contact dermatitis, psoriasis, rheumatoid arthritis, glomerulonephritis, osteoarthritis, lupus erythematosis, scleroderma, asthma, irritable bowel disease and systemic inflammatory response syndrome, e.g. septic shock.

The compounds of Formula I, where possible, are advantageously utilized as the free acid or in the form of a pharmaceutically acceptable salt with various inorganic or organic bases. Typical salts include the alkali metal or alkaline earth salts, although it will be appreciated that other nontoxic salts can also be used. Advantageously, compounds suitable for use in the method of this invention are administered as sodium, potassium, choline or ethylenediamine salts. Sodium salts are preferred.

The compounds of Formula I can be administered in the form of pharmaceutical compositions which comprise, as an active ingredient, at least one compound of Formula I or a pharmaceutically acceptable salt thereof together with a pharmaceutically acceptable carrier. The active ingredient is present in the composition in an amount sufficient to produce an anti-inflammatory effect. The composition of the invention can be formulated so as to be suitable, for example, for oral, nasal, parenteral, topical, transdermal or rectal administration. The compositions can also be formulated so as to be suitable for veterinary use. The composition can take the form of a tablet (preferably enteric coated), capsule (preferably enteric coated), powder, troche, lozenge, inhalant, syrup, emulsion, gel, ointment, cream, lotion, transdermal patch, suppository, sterile injectable liquid as well as liquid suspension or solution. The pharmaceutical compositions of the present invention are prepared by conventional techniques such as by mixing, granulating and compressing or dissolving the ingredients as may be appropriate for the desired preparation.

Preferably, the pharmaceutical composition of the invention includes the active ingredient of Formula I in a quantity selected from 25 mg to 500 mg, advantageously from about 50 mg to 250 mg per dosage unit, depending on the route of administration. Appropriate concentrations and dosage unit sizes can be readily determined by one skilled in the art.

The pharmaceutical carriers used in the composition of the invention may be, for example, in solid or liquid form. Exemplary of solid carriers are lactose, magnesium stearate, terra alba, sucrose, talc, stearic acid, gelatin, agar, pectin or acacia. The amount of solid carrier present in the composition will vary greatly but preferably will be from about 25 mg to 1 g per dosage unit. Exemplary of liquid carriers are syrup, peanut oil, olive oil, sesame oil, propylene glycol, polyethylene glycol (mol wt 200–400), water and saline solution. The carrier or diluent may include a time delay material well known to the art such as, for example, glyceryl monostearate or glyceryl distearate, alone or with a wax. The compositions of the invention may also include any other known pharmaceutical excipients in conventional amounts.

Use of the Invention

The method of treating an inflammatory condition according to this invention comprises administering to a subject in need of such treatment an amount of at least one compound of Formula I sufficient to produce an anti-inflammatory effect. The compounds of Formula I can be administered orally, nasally, topically, transdermally, parentarally (i.v., j.p., i.m. or s.c.), buccaly or analy, as may be required to effect the desired anti-inflammatory effect.

The, active ingredient of Formula I will normally be administered in a dosage selected from about 0.1 mg to 50 mg per kg of body weight, preferably from about 0.5 mg to about 25 mg per kg of body weight. Advantageously, equal doses will be administered, preferably between several timesT per day to one time per week. The frequency of administration and the amount of active ingredient to be administered to effect treatment of a particular inflammatory condition can readily be determined by one skilled in the art. For inflammatory conditions of the lungs, an aerosol dispensing system wherein the active medicament is incorporated with Freon® (fluorohydrocarbon) or other inert propellant in an aerosol container is of particular applicability. Such an aerosol system will deliver a metered dose of about 100 mcg to about 650 mcg administered once or twice at a time as needed.

EXAMPLES

The following non-limiting Examples, which are illustrative of the compounds suitable for use in the methods and compositions of the present invention, demonstrate the activity of these compounds as well as methods for their preparation.

Example 1

Synthesis of Benzoic Acid Derivatives of the Invention by Wittig Condensation

Synthesis of 4-(2-Biphenyl)-E-ethenylbenzoic Acid

A solution of 2-biphenylcarboxylic acid (10.0 g; 50.44 mmol) in THF (200 mL) was cooled to 0° C. and treated with 106 mL of a 1.0M solution of borane in THF. The resulting mixture was stirred overnight. After adding 1N HCl until pH=1, the mixture was stirred for 2 hrs and then concentrated. The residue was taken up in ethyl acetate and washed with brine and water; the organic layer was dried, concentrated, and filtered through Celite, eluting with 10% ethyl acetate in hexane to obtain 9.44 g (quantitative yield) of 2-biphenylcarbinol, $^1$H NMR (CDCl$_3$): δ 4.65 (d, 2H); 7.21–7.48 (m, 8H); 7.58 (d, 1H).

Pyridinium chlorochromate (33.14 g; 153.72 mmol) was added in one portion to a solution of the alcohol (9.44 g; 51.24 mmol) in methylene chloride (150 mL). After stirring at room temperature for 2.5 hrs, an additional 150 mL of methylene chloride was added, and the reaction mixture was filtered through Florosil, washing the filter cake with methylene chloride. The flitrate was concentrated to obtain 8.91 g (95%) of 2-biphenylcarboxaldehyde as a yellow oil, $^1$H NMR (CDCl$_3$): δ 7.25–7.51 (m, 7H); 7.61 (t, 1H); 8.04 (d, 1H); 9.91 (s, 1H).

A mixture of 2-biphenylcarboxaldehyde (8.91 g; 48.69 mmol) and methyl 4-(diethyl-phosphonomethyl)benzoate (20.88 g; 73.04 mmol; 1.5 eq) in THF (75 mL) was added to a suspension of NaH (2.92 g of a 60% dispersion in oil; 73.04 mmol) in 75 mL of THF, at 0° C. and under an argon atmosphere. The reaction mixture was stirred for 0.5 hr at 0° C. and 2.5 hr at room temperature. It was quenched with 1N HCl (pH 1 ) and extracted into ethyl acetate. The organic layer was washed with saturated NaHCO$_3$ and brine, dried, and concentrated. The crude product was purified on a flash column, eluting with 10% ethyl acetate in hexane, to obtain 13.5 g (88%) of the ester as a clear oil, $^1$H NMR (CDCl$_3$): δ 3.89 (s, 3H); 7.05 (d, J=16.3, 1H); 7.22 (d, J=15.9, 1H); 7.35–7.44 (m, 10H); 7.75 (d, J=6.4, 1H); 7.95 (d, J=8.4, 2H).

A solution of the above ester (2.99 g; 9.21 mmol) in THF (45 mL) was treated with a solution of lithium hydroxide monohydrate (1.16 g; 27.62 mmol) in 28 mL of water, followed by 15 mL of methanol. The mixture was heated to 50° C. for 3 hrs, cooled, and the volatiles removed under reduced pressure. Water (100 mL) was added, and the aqueous phase was washed twice with ether, acidified (pH 1) and extracted with ethyl acetate (2X). The combined organic extracts were washed with water, dried and concentrated to yield 4-[2-(2-Biphenyl)-E-ethenyl]benzoic acid as a white solid material (2.30 g; 83%), mp 203.5°–204.5° C., $^1$H NMR (CDCl$_3$): δ 7.08 (d, J=16.3, 2H); 7.25 (d, J=16.3, 2H); 7.38–7.48 (m, 10H); 7.78 (m, 1H); 8.03 (d, J=8.4, 2H). Anal. Calcd. for C$_{21}$H$_{16}$O2: C, 83.98; H, 5.37. Found: C, 83.85; H, 5.42.

Procedure for the Synthesis of Aldehydes via Directed Lithiation/Reaction with N,N-dimethylformamide (Scheme II).

2-phenoxybenzaldehyde: At room temperature, under an argon atmosphere, n-butyllithium (15.45 mL of a 2.5M solution in hexanes, 38.61 mmol) was added to a solution of diphenyl ether (5.0 g; 29.38 mmol) in 100 mL of ether, and the reaction mixture was gently refluxed for 4 hrs. After cooling to 0° C., N,N-dimethylformamide (22.73 mL; 0.293 mol) was added dropwise and the reaction was stirred for 15 min at 0° C. and 1.5 hr at room temperature. After adding 10% H$_2$SO$_4$ to pH 1, it was stirred for 15 min and extracted into ethyl acetate. Chromatography of the crude product (10% ethyl acetate/hexane) provided 4.0 g (69%) of the aldehyde, $^1$H NMR (CDCl$_3$): δ 6.97 (d, 1H); 7.02–7.11 (m, 2H); 7.18–7.22 (m, 2H); 7.29 (t, 1H); 7.39 (t, 1H); 7.43 (t, 1H); 7.95 (t, 1H).

Procedure for Synthesis of Aldehydes via Aryl Bromides (Scheme III).

A mixture of 2-bromophenol (1.50 g; 8.67 mmol), benzyl bromide ( 1.48 mg; 8.65 mmol). potassium carbonate (1.44 g; 10.41 mmol) and sodium iodide (catalytic amount) in 50 mL of acetonitrile was refluxed for 24 hours. After cooling, the solids were filtered off and the filtrate was concentrated. The crude residue was purified on a silica gel column (10% ethyl acetate hexane) to obtain 2.30 g (quantitative yield) of 2-benzyloxybromo- benzene, $^1$H NMR (CDCl$_3$): δ 5.16 (s, 2H); 6.84 (t, 1H, J=7.6); 6.93 (d, 1H, J=8.3); 7.21–7.49(m, 6H); 7.56 (d, 1H, J=7.8).

A solution of the above bromide ( 1.02 g; 3.88 mmol) in 20 mL of THF was cooled to −78° C. and treated with 2.5 eq. of tert-butyllithium. After stirring for 2 min., DMF (6.2 g; 85 mmol) was added via syringe, and the mixture was warmed to room temperature and stirred for 2 hrs. 10% H$_2$SO$_4$, 100 mL, was added, and the mixture was stirred for 20 min before extracting into ethyl acetate. Chromatography of the crude product (10% ether/hexane) delivered 0.77 g of aidehyde, 93% yield, $^1$H NMR (CDCl$_3$): δ 5.19 (s, 2H); 7.06 (d, 2H, J=7.9); 7.35–7.46 (m, 5H); 7.54 (m, 1H); 7.86 (d, 1H, J=7.9); 10.56 (s, 1H).

Procedure for the Synthesis of 2-(1-indolyl)benzaldehyde (Scheme IV)

A mixture of indole (4.16 g; 35.53 mmol), methyl 2-bromobenzoate (2.64 g; 35.53 mmol), potassium carbonate (5.50 g) and CuO (2.0 g) in 40 mL of DMF was refluxed uncler an argon atmosphere for 3.5 hrs. The crude material obtained upon extraction into ethyl acetate and removal of the solvent was purified on a silica gel column (10% ethyl acetate/hexane) to obtain 4.20 g (47%) of methyl 2-(1-indolyl)benzoate, $^1$H NMR (CDCl$_3$): δ 3.45 (s, 3H); 6.43 (d, 1H); 6.99–7.20 (m, 4H); 7.35–7.42 (m, 2H); 7.60 (m, 2H); 7.88 (d, 1H).

The above ester was reduced to 2-( 1-indolyl)benzyl alcohol with lithium aluminum hydride in tetrahydrofuran, yield 100%, $^1$H NMR (CDCl$_3$): δ 4.35 (s, 2H); 6.65 (d, 1H);

7.12 (m, 1H); 7.15–7.19 (m, 2H); 7.20–7.23 (m, 1H); 7.30 (d, 1H); 7.35–7.42 (m,2H); 7.62 (m, 2H).

This alcohol was oxidized to 2-(1-indolyl)benzaldehyde with PCC as previously described, 86% yield, $^1$H NMR (CDCl$_3$): δ 1H); 7.12–7.25 (m, 4H); 7.42 (d, 1H); 7.55 (t, 1H); 7.61–7.72 (m, 2H); 8.06 (d, 1H); 9.65 (s, 1H).

Preparation of 2-[(meta, para-dichloro)benzyl]benzaldehyde (Scheme V)

To a solution of N-methylbenzamide (2.0 g; 14.8 mmol) in 20 mL of THF was added n-butyllithium (14.8 mL of a 2.5M solution in hexane, 37 mmol). After the addition was complete the mixture was refluxed for 15 min and then cooled in an ice-bath. A solution of 3,4-dichlorobenzaldehyde (4.14 g; 23.68 mmol) in 20 mL of ether was added, and the resulting mixture was stirred for 20 min at 0° C. and 1 hr at room temperature. It was poured into 20 mL of 2M H$_2$SO$_4$ and 10 g of ice. The layers were separated and the organic layer was washed with water and brine, dried, and concentrated. The residue was chromatographed, eluting with 5% ethyl acetate/hexane, to obtain 400 mg (9.68%) of 3(meta,para-dichloro)phenylphthalide, $^1$H NMR (CDCl$_3$): δ 6.34 (s, 1H); 7.14 (d, 1H, J=8.3); 7.33–7.38 (m, 2H); 7.46 (d, 1H, J=8.2); 7.58 (t, 1H, J=7.4); 7.69 (t, 1H, J=6.5); 7.97 (d, 1H, J=7.6).

To a cooled (0° C.) solution of the above phthalide and triethylsilane (0.70 mL; 3 eq.) in 1.5: mL of CH$_2$Cl$_2$ was added a solution of TiCl$_4$ in CH$_2$Cl$_2$ (1.80 mL of a 1.0M solution). The red solution was stirred at room temperature for 3 hrs. Excess solvent/reagents were removed under vacuum and water, 20 mL, was added, and the product was partitioned between ether and saturated sodium bicarbonate. The alkaline aqueous phase was acidified and extracted into ether; the ether extracts were washed with water and concentrated to deliver 0.36 g (90%) of 2-[(meta, para-dichloro)benzyl]benzoic acid, $^1$H NMR (CDCl$_3$): δ 4.32 (s, 2H); 7.10 (d, 1H, J=8.4); 7.32–7.39 (m, 2H); 7.49–7.51 (m, 2H); 7.83 (d, 1H, J=7.5).

The above acid was reduced to the alcohol with diborane, in the manner previously described, to obtain 2-[(meta, para-dichloro)benzyl]benzyl alcohol in 76% yield, $^1$H NMR (CDCl$_3$): δ 4.05 (s, 2H); 4.64 (s, 2H); 6.97 (d, 1H, J=8.2); 7.14 (m, 1H); 7.18–7.30 (m, 4H); 7.33 (d, 1H, J=8.2).

The above alcohol was oxidized to the aldehyde using PCC, in 97% yield, $^1$H NMR (CDCl$_3$): δ 4.40 (s, 2H); 7.00 (dd, 1H, J=2, 8.3); 7.21–7.26 (m, 2H); 7.33 (d, 1H, J=8.1); 7.48 (t, 1H, J=7.4); 7.55–7.59 (m, 1H); 7.85 (dd, 1H, J=1.3, 8.9); 10.15 (s, 1H).

Using the appropriate aldehyde and diethylphosphono derivative, the procedure of this example was employed to prepare the following esters:

Methyl E-4-[2-(2-phenoxyphenyl)ethenyl]benzoate, 82%, $^1$H NMR (CDCl$_3$): δ 3.91 (s, 3H); 6.88 (d, 1H); 6.92 (d, 2H); 7.05–7.31 (m, 3H); 7.35 (m, 3H); 7.57 (m, 3H); 7.71 (d, 1H); 7.96 (d, 2H).

Methyl E-4-[2-(2-bromo-5-chlorophenyl)ethenyl]benzoate, 85%, 1H NMR (CDCl$_3$): δ 3.89 (s, 3H); 7.18 (m, 2H); 7.36–7.61 (m, 5H); 8.01 (d, 2H).

Methyl E-4-[2-(phenylmercaptophenyl)ethenyl]benzoate, 71%, $^1$H NMR (DMSO-d$^6$): δ3.82 (s, 3H); 7.15–7.37 (m, 9H); 7.49 (d, 2H); 7.63 (d, 1H); 7.89 (m, 2H).

Methyl E-4-[2-(benzoaminophenyl)ethenyl]benzoate, 69%, $^1$H NMR (CDCl$_3$): δ 3.80 (s, 3H); 5.58 (br, 1H); 6.91 (t, 2H); 7.02 (d, 2H); 7.10 (dd, 2H); 7.29 (m, 2H); 7.39 (dd, 1H); 7.46 (d, 2H); 7.60 (d, 2H); 8.02 (d, 2H).

Methyl E-4-[2-(2'-benzylphenyl)ethenyl]benzoate, 49%, $^1$H NMR (DMSO-d$^6$): δ 3.83 (s, 3H); 4.15 (s, 2H); 6.99–7.23 (m, 9H); 7.60–7.63 (m, 3H); 7.69 (m, 1H); 7.82 (d, 2H).

Methyl E-4-[2-(2-bromophenyl)ethenyl]benzoate, 90%, $^1$H NMR (CDCl$_3$): δ 3.91 (s, 3H); 7.28 (t, 1H); 7.53 (dd, 4H); 7.65 (d, 1H); 7.99 (d, 2H).

Methyl 4-[2-{ 2-Methylphenoxy}phenyl-(E)-ethenyl]benzoate, 31%, $^1$H NMR (CDCl$_3$): δ 3.92 (s, 3H); 5.19 (s, 2H); 6.99–7.09 (m, 3H); 7.30–7.41 (m, 4H); 7.46–7.52 (m, 3H); :7.70 (d, 1H, J=7.9); 7.98 (d, 2H, J=8.4).

Methyl 4-[2-(2-benzyloxyphenyl)-(E)-ethenyl]benzoate, 96%, $^1$H NMR (CDCl$_3$): δ 3.92 (s, 3H); 5.17 (s, 2H); 6.95–7.01 (m, 2H); 7.16–7.43 (m, 7H); 7.53 (d, 2H, J=8.4); 7.61–7.65 (m, 2H); 8.00 (d, 2H, J=8.4).

Methyl 4-[2-(2-{1-indolyl}phenyl)-(E)-ethenyl]benzoate, not isolated.

Methyl 4-[2-(2-Methylthiophenyl)-(E)-ethenyl]benzoate, not isolated.

Methyl 2-[2-(-2-{meta,para-dichloro}benzyl)phenyl-(E)-ethenyl]benzoate, 54%, $^1$H NMR (CDCl$_3$): δ 3.92 (s, 3H); 4.09 (s, 2H); 6.99 (m, 2H); 7.16 (d, 1H, J=7.1) 7.24–7.35 (m, 6H); 7.45 (d, 2H, J=8.3); 7.66 (d, 1H, J=7.2); 8.00 (d, 2H, J=8.3)

Hydrolysis of the appropriate esters as described furnished the following compounds of the invention:

4-[2-(2-{1-Phenyl}pyrrolyl)-E)-ethenyl]benzoic acid, mp 236°–238° C., $^1$H NMR (DMSO-d$^6$): δ 6.30 (1H, t, J=3.2); 6.77 (1H, dd, J=1.5, 3.7); 6.98, 6.92 (AB q, 2H J=16.3); 7.08 (dd, 1H, J=1.6, 2.5); 7.35–7.57 (m, 5H); 7.83 (d, 2H, J=8.4); 12.81 (br, 1H).

2'-Phenoxy-4-stilbenecarboxylic acid, 87%, mp 237° C., $^1$H NMR (DMSO-d$^6$): δ 6.93 (d, 2H); 6.98 (d, 2H); 7.10 (t, 1H); 7.22 (t, 1H); 7.40 (m, 4H); 7.60 (d,2H); 7.88 (d, 4H); 12.90 (s, 1H). IR (nujol): 2914, 2855, 1674, 1589, 1454, 1378, 1286 cm$^{-1}$ Anal. Calcd. for C$_{21}$H$_{16}$O$_3$: C, 79.73; H, 5.10. Found: C, 79.56; H, 5.12.

2'-Phenylmercapto-4-stilbenecarboxylic acid, 50%, mp 224°–225° C., $^1$H NMR (DMSO-d$^6$): δ 7.21–7.45 (m, 9H); 7.58–7.60 (m, 2H); 7.68–7.72 (m, 1H); 7.90–7.92 (m, 2H); 12.94 (s, 1H). IR (KBr): 2968, 2810, 2672, 2540, 1676, 1598, 1421, 1289, 1177 cm$^{-1}$. Anal. Calcd. for C$_{21}$H$_{16}$O$_2$S: C, 75.88; H, 4.85; S, 9.64. Found: C, 75.79; H, 4.84; S, 9.74.

2'-Benzyl-4-stilbenecarboxylic acid, 50%, mp 199°–200° C., $^1$H NMR (DMSO-d$^6$): δ 4.18 (s, 2H); 7.11–7.29 (m, 9H); 7.61–7.67 (m, 3H); 7.73–7.75 (m, 1H); 7.89–7.92 (m, 2H); 12.91 (s, 1H). IR (KBr): 2827, 2547, 1674, 1596, 1425, 1284, 1175, 941 cm$^{-1}$. Anal. Calcd. for C$_{22}$H$_{18}$O$_2$— 0.1 H$_2$O: C, 83.57; H, 5.80. Found: C, 83.59; H, 5.88.

4-[2-(2-phenoxymethyl)phenyl-E-ethenyl]benzoic acid, 83%, mp 178° C., $^1$H NMR (DMSO-d$^6$): δ 5.30 (s, 2H); 6.96 (t, 1H, J=7.3); 7.06 (d, 2H, J=8.2); 7.26–7.36 (m, 4H); 7.40 (t, 1H, J=7.6); 7.52 (d, 1H, J=7.5); 7.59–7.68 (m, 3H); 7.82 (d, 1H, J=7.6); 7.90 (d, 2H, J=8.3); 12.93 (br, 1H). Anal. Calcd. for C$_{22}$H$_{18}$O$_3$: C, 79.98; H, 5.49. Found: C, 79.87; H, 5.55.

4-[2-(2-benzyloxy)phenyl-(E)-ethenyl]benzoic acid, 25%, mp 163°–165° C. $^1$H NMR (DMSO-d$^6$): δ 5.22 (s, 2H); 6.98 (t, 1H, J=7.5); 7.11 (d, 1H, J=8.3); 7.24–7.36 (m, 6H); 7.39 (d, 2H, J=7.7); 7,48–7.62 (m, 2H); 7.69 (d, 1H, J=7.6); 7.92 (d, 1H, J=8.2); 12.91 (br, 1H). Anal. Calcd. for C$_{22}$H$_{18}$O$_3$: C, 79.98; H, 5.49. Found: C, 79.77; H, 5.52.

4-[2-{2-(meta, para-dichloro)benzyl}-E)-ethenyl]benzoic acid, 100%, mp>210° C. (dec), $^1$H NMR (DMSO-d$^6$): δ 4.22 (s, 2H); 7.15 (m, 2H); 7.29 (m, 3H); 7.49 (m, 2H); 7.60 (d, 1H, J=16.4); 7.68 (d, 2H, J=8.3); 7.74 (d, 1H); 7.91 (d, 2H, J=8.3); 12.91 (br, 1H). Anal. Calcd. for $C_{22}H_{16}O_2Cl_2$: C, 68.94; H, 4.21. Found: C, 68.84; H, 4.27.

4-[2-(2-Methylthiophenyl)-(E)-ethenyl]benzoic acid, 25%, mp 190°–191° C., $^1$H NMR (CDCl$_3$): δ 4.22 (s, 3H); 6.98 (d, 1H, J=16.3); 7.15–7.7.33 (m, 9H); 7.50 (m, 2H); 7.58 (d, 1H); 8.05 (d, 2H). Anal. Calcd. for $C_{22}H_{18}O_2S$: C, 76.27; H, 5.24; S, 9.25. Found: C, 76.21; H, 5.19; S, 9.33.

Example 2

Synthesis of 4-[2-(2-biphenyl)ethyl]benzoic Acid

A solution of methyl 4-[(2-biphenyl)-E-ethenyl]benzoate (2.99 g; 9.49 mmol) in ethanol (60 mL) was treated with 10% palladium on carbon (1.0 g) and hydrogenated in a Parr shaker at 50 psi overnight. The solution was filtered through Celite to obtain 2.78 g (92%) of the reduced compound as an oil, $^1$H NMR (CDCl$_3$): δ 2.71–2.80 (m, 2H); 2.82–2.93 (m, 2H); 3.93 (s, 3H); 6.93 (d, 2H); 7.18–7.23 (m, 5H); 7.25–7.41 (m, 3H); 7.85 (d, 2H).

The above ester was hydrolyzed as previously described to furnish 4-[2-(2-biphenyl)ethyl]benzoic acid as a white solid (89%), mp 159.5°–160.5° C., $^1$H NMR (DMSO-d$^6$): δ 2.74–2.78 (m, 2H); 2.89–2.93 (m, 2H); 6.99 (d, J=8.2, 2H); 7.21–7.43 (m, 9H); 7.92 (d, J=8.2, 2H). Anal. Calcd. for $C_{21}H_{18}O_2$: C, 83.42; H, 6.0. Found: C, 83.25; H, 6.09.

Reduction of the appropriate olefinic esters gave the following dihydro compounds:

Methyl 4-[2-(phenoxyphenyl)ethyl]benzoate, 95%, $^1$H NMR (CDCl$_3$) δ 2.87 (s, 4H); 3.81 (s, 3H); 6.83 (t, 1H); 6.96 (t, 1H); 7.09 (m, 4H); 7.23 (t, 2H); 7.82 (d, 2H).

Methyl 4-[2-(benzeneaminophenyl)ethyl]benzoate, 95%, $^1$H NMR (CDCl$_3$): δ2.92 (dm, 4H); 3.91 (s, 3H); 5.11 (br, 1H); 6.75 (d, 2H); 6.82 (t, 1H); 6.95 (t, 1H); 7.18 (m, 7H); 7.97 (d, 2H).

The above esters were hydrolyzed as previously described to the following products as white solids:

4-[2-(2'-Phenoxyphenyl)ethyl]benzoic acid, 52%, mp 135°–137° C., $^1$H NMR (CDl$_3$): δ 2.49 (m, 4H); 6.89 (m, 3H); 7.09 (m, 2H); 7.21 (m, 3H); 7.34 (m, 3H); 7.79 (d, 2H, J=8.2); 12.80 (br, 1H). IR (nujol): 2923, 1674, 1454, 1370, 1294, 1226, 745 cm$^{-1}$. Anal. Calcd. for $C_{21}H_{18}O_3$: C, 79.23; H, 5.70. Found: C, 79.21; H, 5.73.

N-Phenyl-1-[(p-carboxyphenyl)ethyl]aniline, 86%, mp 172°–173° C., $^1$H NMR (CDCl$_3$): δ 2.88 (s, 4H); 6.70 (t, 1H); 6.83 (d, 2H); 6.93 (t, 1H); 7.15 (m, 4H); 7.28 (d, 2H); 7.45 (d, 1H); 7.80 (d, 2H); 12.79 (s, 1H). IR (nujol) 2923, 2855, 1682, 1589, 1488, 1454, 1378, 1294 cm$^{-1}$. Anal. Calcd. for $C_{21}H_{19}NO_2$: C, 79.47; H, 4.41. Found: C, 79.24, H, 4.32.

Example 3

Synthesis of 4-[2-(2-{2-thienyl}phenyl)-(E)-ethenyl]benzoic Acid

To a stirred solution of 1.96 g (12.0 mmol) of 2-bromothiophene in 100 mL of THF at –78° C. was added 5.2 mL (13.0 mmol) of 2.5M n-butyllithium in hexane. The mixture was stirred for 15 min at –78° C. and then 4.23 g (13.0 mmol) of tributyltin chloride was added. The stirred mixture was allowed to warm to room temperature and stirring was continued for 20 minutes. After removing the solvent under reduced pressure, the solution was diluted with water and the resulting mixture was extracted with ether. The ether extracts were washed with water, dried and concentrated. The residue was chromatographed, eluting with hexane, to obtain 4.11 g; 91%) of 2-(tributylstannyl)thiophene as a, colorless liquid.

To a stirred solution of 0.74 g (2.33 mmol) of methyl E-4-[2-(2bromophenyl)ethenyl]-benzoate (Example 1 ) and 0.91 g of the above tributyltin reagent in 25 mL of dioxane containing a catalytic amount of 2,6-di-tert-butyl-4-methylphenol, under argon, was added 100 mg of tetrakis(triphenylphosphine)palladium (0). After the reaction mixture was heated under reflux for 3 hrs, it was allowed to cool to room temperature and diluted with 150 mL of ether, to the mixture was added 40 mL of water. The organic layer was separated, washed with brine, dried, and concentrated. The crude residue was flash chromatographed (5% ethyl acetate in hexane) to afford 0.73 g (98%) of methyl 4-[2-(2-{2-thienyl}phenyl)-(E)-ethenyl]benzoate as a colorless liquid, $^1$H NMR (CDCl$_3$): δ 3.91 (s, 3H); 7.15 (m, 3H); 7.30–7.41 (m, 3H); 7.43 (m, 4H); 7.72 (d, 1H); 7.95 (d, 2H).

The above ester was hydrolyzed as described in Example 1 to afford 4-[2-(2-{2-thienyl}phenyl)-(E)-ethenyl]benzoic acid as white crystals (98%), mp 208°–210° C., $^1$H NMR (DMSO-d$^6$): δ 7.17 (m, 2H); 7.25 (d, 1H, J=16.3); 7.36–7.48 (m, 4H); 7.27 (d, 2H, J=8.3); 7.66 (dd, 1H, J=1.0, 4.3); 7.81 (d, 1H, J=7.2); 7.91 (d, 2H, 8.3); 12.91 (br, 1H). Anal. Calcd. for $C_{19}H_{14}O_2S$—0.33 $H_2O$: C, 73.07; H, 4.73. Found: C, 72.81; H, 4.55.

Using the appropriate aryl stannanes and bromo esters, the overall procedure of this example was employed to prepare the following esters:

Methyl E-4-{2-[2-(2-furanyl)phenyl]ethenyl}benzoate, 90%, $^1$H NMR (CDCl$_3$): δ 3.92 (s, 3H); 6.52 (d, 2H, J=5.3); 7.04 (d, 1H, J=16.2); 7.38 (m, 2H); 7.56 (m, 4H); 7.68 (t, 2H, J=6.9); 8.03 (d, 2H, J=8.4).

Methyl E-4-{2-[2-(2-thiazolyl)phenyl]ethenyl}benzoate, 79%, mp 146°–147° C., $^1$H NMR (CDCl$_3$): δ 3.92 (s, 3H); 7.09 (d, 2H, J=16.2); 7.27–7.49 (m, 6H); 7.75 (d, 1H); 7.91 (s, 1H); 8.01 (d, 2H, J=6.6).

Methyl E-4-{2-[2-(2-thianapthonyl)phenyl]ethenyl}benzoate, 76%, mp 161.5°–163.5° C., $^1$H NMR (CDCl$_3$): δ 3.92 (s, 3H); 7.08 (d, 2H, J=16.3); 7.19–7.55 (m, 8H); 7.60–7.72 (dd, 2H); 7.82 (d, 1H); 8.02 (d, 2H).

Methyl E-4-{2-[2-(2-benzofuranyl)phenyl]ethenyl}benzoate, 25%, $^1$H NMR (DMSO-d$^6$): δ 3.93 (s, 3H); 6.84 (s, 1H); 7.11 (d, 1H, J=16.2); 7.25–7.36 (m, 2H); 7.43–7.55 (m, 2H); 7.55–7.64 (m, 5H); 7.73 (m, 1H); 7.86 (m, 1H); 8.04 (d, 2H, J=8.3).

Methyl E-4-{2-[2-(1-naphthyl)phenyl]ethenyl}benzoate, 58%, 1H NMR (CDCl$_3$): δ 3.93 (s, 3H); 6.82 (d, 1H, J=16); 6.99 (d, 1H, J=16); 7.04 (d, 2H); 7.23–7.48 (m, 8H); 7.80 (m, 5H).

Methyl E-4-{2-[2-(2-naphthyl)phenyl]ethenyl}benzoate, 57%, $^1$H NMR (CDCl$_3$): δ 3.87 (s, 3H); 7.09 (d, 1H, J=16.2); 7.24 (d, 1H, J=16.2); 7.36–7.50 (m, 5H); 7.51–7.55 (m, 3H); 7.79 (d, 1H); 7.85–7.93 (m, 6H).

Methyl E-4-{2-[2-(4-chlorophenyl)phenyl]ethenyl}benzoate, 96%, $^1$H NMR (CDCl$_3$): δ 3.91 (s, 3H); 7.06 (d, 1H, J=16.3); 7.16 (d, 1H, J=16.3);

7.30–7.43 (m, 9H); 7.75 (d, 1H, J=7.4); 7.98 (d, 2H, J=8.4).

Methyl E-4-{2-[2-(4-chlorophenyl)-5-chlorophenyl]ethenyl}benzoate, 70%, $^1$H NMR (CDCl$_3$): δ 3.93 (s, 3H); 7.04 (s, 2H); 7.16–7.30 (m, 2H); 7.42 (dd, 4H); 7.69 (s, 1H); 7.91 (d, 2H).

Methyl E-4-{2-[2-(3,4-dichlorophenyl)phenyl]ethenyl}benzoate, 75%, mp 105.5°–107° C., $^1$H NMR (CDCl$_3$): δ 3.91 (s, 3H); 7.09 (d, 2H, J=17.6); 7.15–7.51 (m, 8H); 7.75 (d, 1H, J=7.8); 7.99 (dd, 2H, J=5.4, 8.4).

Methyl E-4-{2-[2-(3,4-dichlorophenyl)-5-chlorophenyl]ethenyl}benzoate, 59%, $^1$H NMR (CDCl$_3$): δ 3.92 (s, 3H); 7.05 (d, 2H, J=16.1); 7.18 (d, 2H); 7.35 (dd, 1H); 7.39–7.45 (m, 4H); 7.68 (s, 1H); 7.95 (d, 2H).

Methyl E-4-{2-[2-(3,5-dichlorophenyl)phenyl]ethenyl}benzoate. This compound was not characterized but carried directly to the next step.

Methyl E-4-{2-[2-(3,5-(a, a, a-trifluoromethylmethyl)phenyl)phenyl]ethenyl}benzoate. This was not characterized but carried directly to the next step.

Methyl 4-[2-(2-{2-Pyridyl}phenyl)-(E)-ethenyl]benzoate, 41%, $^1$H NMR (CDCl$_3$): δ 3.89 (s, 3H); 6.99 (d, 1H, J=16.3); 7.21–7.38 (m, 7H); 7.45 (d, 1H); 7.63 (m, 2H); 7.88 (d, 1H); 8.78 (d, 1H).

Hydrolysis of the esters as described in Example 1 furnished the following compounds of the invention:

4-{2-[2-(2-furanyl)phenyl]-(E)-ethenyl}benzoic acid, 92%, mp 200°–201° C., $^1$H NMR (DMSO-d$^6$): δ 6.63–6.66 (m, 2H); 7.22–7.95 (m, 11H); 12.93 (s, 1H). Anal. Calcd. for C$_{19}$H$_{14}$O$_3$: C, 78.61; H, 4.86. Found: C, 78.40; H, 4.86.

4-{2-[2-(2-thiazolyl)phenyl]-(E)-ethenyl}benzoic acid, 99%, mp 203°–204° C., $^1$H NMR (DMSO-d$^6$): δ 7.26–7.62 (m, 7H); 7.85–7.98 (m, 4H); 9.21 (s, 1H); 12.93 (br, 1H). Anal. Calcd. for C$_{18}$H$_{13}$O$_2$SN-0.25 H$_2$O: C, 69.32; H, 4.36; N, 4.49; S, 10.30. Found: C, 69.03; H, 4.22; N, 4.42; S, 10.12.

4-[2-[2-(2-thianapthonyl)phenyl]-(E)-ethenyl}benzoic acid, 83%, mp 271°–272° C., $^1$H NMR (DMSO-d$^6$): δ 7.35–7.61 (m, 10H); 7.88–7.91 (m, 4H); 8.00–8.02 (m, 1H) 12.91 (s, 1H). Anal. Calcd. for C$_{23}$H$_{16}$O$_2$S: C, 77.50; H, 4.52; S, 8.99. Found: C, 77.32; H, 4.48; S, 8.97.

4-{2-[2-(2-benzofuranyl)phenyl]-(E)-ethenyl}benzoic acid, 88%, mp 215°–217° C., $^1$H NMR (DMSO-d$^6$): δ7.07 (s, 1H); 7.30 (m, 3H); 7.37 (m, 2H); 7.68 (m, 5H); 7.84 (m, 2H); 7.94 (d, 2H). Anal. Calcd. for C$_{23}$H$_{16}$O$_3$-0.33 H$_2$O: C, 79.76; H, 4.85. Found: C, 79.73; H, 4.72.

4-{:2-[2-(1-naphthyl)phenyl]-(E)-ethenyl}benzoic acid, mp 248°–250° C., $^1$H NMR (DMSO-d$^6$): δ 6.70 (d, 1H, J=16.4); 7.16 (d, 2H, J=8.1); 7.23–8.00 (m, 14H). Anal. Calcd. for C$_{25}$H$_{18}$O$_2$-0.5 H2O: C, 83.54; H, 5.33. Found: C, 83.55; H, 5.31.

4-{2-[2-(2-naphthyl)phenyl]-(E)-ethenyl}benzoic acid, 96%, mp 279°–280° C., $^1$H NMR (DMSO-d$^6$): δ 7.21 (d, 1H, J=16.3); 7.33 (d, 1H, J=16.3); 7.45–7.58 (m, 8H); 7.84 (d, 2H, J=8.3); 7.91–8.01 (m, 5H); 12.88 (s, 1H). Anal. Calcd. for C$_{25}$H$_{18}$O$_2$: C, 85.69; H, 5.18. Found: C, 85.49; H, 5.24.

4-{2-[2-(4-chlorophenyl)phenyl]-(E)-ethenyl}benzoic acid, 30%, mp 237°–238.5° C., $^1$H NMR (DMSO-d$^6$): δ 7.12 (d, 1H, J=16.3); 7.29–7.53 (m, 10H); 7.85–7.89 (m, 3H); 12.90 (s, 1H). Anal. Calcd. for C$_{21}$H$_{15}$O$_2$Cl: C, 75.34; H, 4.52; Cl, 10.59. Found: C, 75.38; H, 4.54; Cl, 10.62.

4-{2-[2-(4-chlorophenyl)-5-chlorophenyl]-(E)-ethenyl}benzoic acid, 95%, 238°–240° C., $^1$H NMR (DMSO-d$^6$): δ 7.05 (d, 1H, J=16.3); 7.34–7.55 (m, 9H); 7.89 (d, 2H, J=8.2); 7.95 (s, 1H); 12.94 (s, 1H). Anal. Calcd. for C$_{21}$H$_{14}$O$_2$Cl$_2$: C, 68.31; H, 3.82; Cl, 19.20. Found: C, 68.28; H, 3.81; Cl, 19.21.

4-{2-[2-(3,4-dichlorophenyl)phenyl]-(E)-ethenyl}benzoic acid, 88%, 248°–249° C., mp °C., $^1$H NMR (CDCl$_3$): δ 7.14 (d, 1H, J=16.3); 7.26–7.49 (m, 5H); 7.54 (d, 2H, J=8.1); 7.61 (s, 1H); 7.71 (d, J=8.3); 7.86–7.90 (m, 3H); 12.89 (s, 1H).

4-{2-[2-(3,4-dichlorophenyl)-5-chlorophenyl]-(E)-ethenyl}benzoic acid, 59%, mp 249°–250° C., $^1$H NMR (DMSO-d$^6$): δ 7.06 (d, 1H, J=16.3); 7.31–7.47 (m, 4H); 7.55 (d, 2H, J=8.3); 7.63 (s, 1H); 7.72 (d, 1H, J=8.2); 7.89 (d, 2H, J=8.3); 7.95 (s, 1H); 12.93 (s, 1H). Anal. Calcd. for C$_{21}$H$_{13}$O$_2$Cl$_3$: C, 62.48H, 3.25; Cl, 26.35. Found: C, 62.47; H, 3.26; Cl, 26.36.

4-{2-[2-(3,5-dichlorophenyl)phenyl]-(E)-ethenyl}benzoic acid, 92%, mp 250°–253° C., $^1$H NMR (DMSO-d$^6$): δ 7.10 (d, 1H, J=16.3); 7.26 (d, 1H, J=16.3); 7.36–7.52 (m, 6H); 7.67 (s, 1H); 7.86–7.90 (m, 4 H). Anal. Calcd. for C$_{21}$H$_{14}$O$_2$Cl$_2$: C, 68.31; H, 3.82; Cl, 19.20. Found: C, 68.08; H, 3.96; Cl, 19.34.

4-{2-[2-(3,5-(a, a, a-trifluoromethylmethyl)phenyl)phenyl]-(E)-ethenyl} benzoic acid, 44%, mp 243°–244° C., $^1$H NMR (DMSO-d$^6$): δ 7.14 (d, 1H, J=16.3); 7.30 (d, 1H, J=16.3); 7.48–7.54 (m, 5H); 7.86–7.92 (m, 3H); 8.04 (s, 2H); 8.17 (s, 1H); 12.93 (s, 1H). Anal. Calcd. for C$_{23}$H$_{14}$O$_2$: C, 63.31; H, 3.23. Found: C, 63.26; H, 3.25.

4-[2-(2-{2-Pyridinyl}phenyl)-(E)-ethenyl]benzoic acid hydrochloride, 82%, mp 199°–200° C., $^1$H NMR (DMSO-d$^6$): δ 7.23–7.54 (m, 9H); 7.88–7.92 (m, 4H); 8.71 (d, 1H, J=4.1). Anal. Calcd. for C$_{20}$H$_{15}$NO$_2$-HCl-0.2 H$_2$O: C, 70.36; H, 4.84; N, 4.10. Found: C, 70.25; H, 4.48; N, 4.10.

Synthesis of
4-[3-(4-benzoxyphenyl)-propoxy]benzoic Acid
(Scheme VIII)

A mixture of 2-bromo-O-benzyl phenol (*J. Med. Chem.* (1992) 35:3483) (2.17 g; 8.25 mmol), methyl acrylate (0.83 g; 9.9 mmol), dichloropalladium(II)bis(triphenylphosphine) (150 mg) and triethylamine (2.51 g; 24.7 mmol) in 10 mL of DMF was heated in a sealed tube to 120° C. for 16 hrs. After cooling, the tube's contents were partitioned between ethyl acetate and water. Removal of the organic solvent and purification on silica gel (20% ethyl acetate/hexane) afforded 1.22 g (55%) of methyl 2-benzoxycinnamate, $^1$H NMR (CDCl$_3$): δ 3.78 (s, 3H); 5.15 (s, 2H); 6.54 (d, 1H, J=16.2); 6.95 (m, 2); 7.33–7.41 (m, 6H); 7.52 (d, 1H, J=7.7).

The above acrylate was hydrogenated as previously described to provide methyl 2-benzoxyclehydrocinnamic acid, 95%, $^1$H NMR (CDCl$_3$): δ2.65 (t, 2H, J=7.4); 3.00 (t, 2H, J=7.6); 3.64 (s, 3H); 5.09 (s, 2H); 6.89 (m, 2H); 7.16–7.23 (m, 2H); 7.33–7.43 (m, 5H).

This ester was reduced to the alcohol with lithium aluminum hydride, as described previously, to obtain (2-benzoxy)-3-phenylprop-1-ol, 87%, $^1$H NMR (CDCl$_3$): δ1.81 (m, 3H); 2.77 (t, 2H, J=7.3); 3.57 (t, 2H, J=6.3); 5.07 (s, 2H); 6.89–6.93 (m, 2H); 7.14–7.18 (m, 2H); 7.32–7.44 (m, 5H).

A mixture of the above alcohol (0.78 g; 3.22 mmol), methyl 4-hydroxybenzoate (0.74 g; 4.83 mmol) and triphenylphosphine (1.01 g; 3.86 mmol) in 15 mL of THF was treated with diisopropylazodicarboxylate (0.72 g; 3.54 mmol) and stirred at room temperature for 24 hours. The product was extracted into ethyl acetate; the organic phase was washed with water, dried and chromatographed (10% ethyl acetate/hexane) to afford 900 mg (74%) of methyl 4-[3-(4-benzoxyphenyl)propoxy]benzoate, $^1$H NMR (CDCl$_3$): δ 2.13 (m, 2H); 2.87 (t, 2H, J=7.8); 3.89 (s, 3H); 4.00 (t, 2H, J=6.4); 5.07 (s, 2H); 6.83–6.86 (m, 4H); 6.91 (d, 2H, J=7.3); 7.34–7.44 (m, 5H); 7.95 (d, 2H, J=6.9).

Hydrolysis of this ester as previously described furnished 4-[3-(4-benzoxyphenyl)propoxy]benzoic acid, 57%, mp 128.5°–129.5° C., $^1$H NMR (DMSO-d$^6$): δ 2.04–2.17 (m, 2H); 2.88 (t, 2H, J=7.3); 4.02 (t, 2H, J=6.4); 5.07 (s, 2H); 6.86–7.44 (m, 11H); 8.02 (d, 2H, J=8.9). Anal. Calcd. for $C_{23}H_{22}O_4$-0.25 $H_2O$: C, 75.29; H, 6.18. Found: C, 75.25; H, 6.05.

Using the Mitsunobu coupling procedure and the appropriate alcohol with methyl 4-hydroxybenzoate, the following esters were prepared:

Methyl 4-[3-(2-biphenyl)methoxy]benzoate, 32%, $^1$H NMR (CDCl$_3$): δ 3.86 (s, 3H); 4.98 (s, 2H); 6.85 (d, 2H, J=9.0); 7.33–7.42 (m, 8H); 7.59 (m, 1H); 7.93 (d, 2H, J=9.0).

Methyl 4-[2-(2-biphenyl)ethoxy]benzoate, 88%, $^1$H NMR (CDCl$_3$): δ 3.08 (t, 2H); 3.82 (s, 3H); 4.03 (t, 2H); 6.68 (d, 2H); 7.21–7.48 (m, 9H); 7.87 (d, 2H).

Methyl 4-[5-(2-biphenyl)pentoxy]benzoate, 96%, 1H NMR (CDCl$_3$): δ 1.32–1.38 (m, 2H); 1.41–1.51 (m, 2H); 1.62–1.68 (m, 2H); 2.60 (m, 2H); 3.93 (s, 3H); 6.81 (d, 2H); 7.18–7.39 (m, 9H); 7.99 (d, 2H).

The above esters were hydrolyzed to provide the following examples of the invention:

4-[3-(2-Biphenyl)methoxy]benzoic acid, 46%, mp 158°–159° C., $^1$H NMR (DMSO-d$^6$): δ 5.00 (s, 2H); 6.88 (d, 2H, J=8.9); 7.60 (m, 1H); 7.33–7.43 (m, 8H); 8.01 (d, 2H, J=9.0). Anal. Calcd. for $C_{20}H_{16}O_3$: C, 78.93; H, 5.30. Found: C, 78.78; H, 5.33.

4-[2-(2-biphenyl)ethoxy]benzoic acid, 22%, mp 138°–139° C., $^1$H NMR (DMSO-d$^6$): δ 3.09 (t, 2H, J=7.2); 4.02 (t, 2H, J=7.3); 6.67 (d, 2H, J=8.6); 7.19–7.42 (m, 9H); 7.95 (d, 2H, J=8.6); 11.86 (s, 1H). Anal. Calcd. for $C_{21}H_{18}O_3$: C, 79.23; H, 5.70. Found: C, 79.03; H, 5.69.

4-[5-(2-biphenyl)pentoxy]benzoic acid, 82%, mp 111.5°–112.5° C., $^1$H NMR (DMSO-d$^6$): δ 1.32–1.39 (m, 2H); 1.48–1.55 (m, 2H); 1.63–1.70 (m, 2H); 2.62 (t, 2H, J=7.8); 3.88 (t, 2H, J=6.5); 6.87 (d, 2H, J=8.8); 7.19–7.49 (m, 9H); 8.04 (d, 2H, J=8.8). Anal. Calcd. for C24H24O3: C, 79.97; H, 6.71. Found: C, 79.91; H, 6.74.1

Synthesis of 4-[4-(2-Phenoxypropyl)-but-1-(E)-enyl]benzoic Acid (Scheme IX)

A mixture of 2-phenoxybenzaldehyde (2.12 g; 10.70 mmol) and methyl (triphenylphos-phoranylidene)acetate (4.01 g; 11.76 mmol) in 60 mL of THF was refluxed overnight. The reaction was cooled, diluted with ethyl acetate (50 mL) and washed with water (3X). The crude residue was purified on a silica gel column eluting with hexane to obtain 1.4 g (52%) of 2-phenoxycinnamic acid, $^1$H NMR (CDCl$^3$): δ 3.78 (s, 3H); 6.56 (d, 1H, J=16.1); 6.87 (d, 1H, J=8.5); 7.00 (d, 2H, J=7.5); 7.10–7.15 (m, 2H); 7.28–7.33 (m, 3H); 7.36 (d, 1H, J=8.5); 8.02 (d, 2H, J=16.2).

The above compound was hydrogenated as previously described to furnish 2-phenoxydihydrocinnamic acid in 100% yield, $^1$H NMR (CDCl$_3$): δ 2.65 (t, 2H, J=7.1); 2.98 (t, 2H, J=7.5); 3.63 (s, 3H); 6.85 (d, 1H, J=7.9); 6.95 (m, 2H); 7.05–7.16 (m, 2H); 7.28 (m, 2H); 7.31 (m, 2H).

This ester was reduced with lithium aluminum hydride as previously described to afford 4-[(2-phenoxy)phenyl]prop-1-ol, 88%, $^1$H NMR (CDCl$_3$): δ 1.86 (m, 2H); 2.75 (m, 2H); 3.63 (m, 2H); 6.82–6.90 (m, 3H); 6.99–7.05 (m, 2H); 7.10–7.18 (m, 1H); 7.21–7.25 (m, 2H).

This alcohol was oxidized to the aldehyde as previously described to obtain 4-[(2-phenoxy)phenyl]-1-propanal, $^1$H NMR (CDCl$_3$): δ 2.78 (t, 2H); 2.99 (t, 2H, J=7.6); 6.86 (d, 1H); 6.93–6.95 (m, 2H); 7.05–7.10 (m, 2H); 7.16–7.21 (m, 1H); 7.26–7.34 (m, 3H); 9.79 (s, 1H).

Methyl 4-[4-(2-phenoxy)phenyl-but-1-(E)-enyl]benzoate, 47%, was synthesized from the above aldehyde by Wittig reaction in the manner previously described, $^1$H NMR (CDCl$_3$): δ 2.57 (2H); 2.83 (m, 2H); 3.90 (s, 3H); 6.37 (m, 2H); 6.89–6.94 (m, 3H); 7.06–7.18 (m, 2H); 7.26 (m, 1H); 7.28–7.35 (m, 5H); 7.94 (d, 2H, J=6.6).

Hydrolysis of the above ester furnished 4-[4-(2-phenoxy)phenyl-but-1-(E)-enyl]benzoic acid, 84%, mp 198°–200° C., 1H NMR (DMSO-d$^6$): δ 2.74 (t, 2H); 3.31 (d, 2H); 6.43 (m, 2H); 6.88 (m, 3H); 7.09 (m, 2H); 7.22 (t, 1H); 7.34 (m, 3H) 7.43 (d, 2H); 7.83 (d, 2H). Anal. Calcd. for $C_{22}H_{18}O_2$-0.25 $H_2O$: C, 79.18; H, 5.92. Found: C, 79.17; H, 5.95.

Reduction of the above compound by catalytic hydrogenation furnished 4-[4-(2-phenoxyphenyl)butyl]benzoic acid, 88%, mp 120° C., 1H NMR (DMSO-d$^6$): δ 1.54 (m, 4H); 2.53 (m, 4H); 6.83 (m, 3H); 7.07 (m, 2H); 7.25 (m, 6H); 7.79 (d, 2H). Anal. Calcd. for $C_{23}H_{22}O_3$-0.25 $H_2O$: C, 78.72; H, 6.46. Found: C, 78.68; H, 6.49.

In Vitro Assays

Several in vitro assays were employed to determine the ability of compounds of the invention to function as antiinflammatory agents. One group of assays measured the ability of the compounds to inhibit adherence of polymorphonuclear neutrophils to serum coated wells (in the presence of either TNF-α or PAF) or to human umbilical vein endothelial cells (in the presence of INF-γ). Another group of assays measured the ability of the compounds to inhibit the release of elastase or superoxide from activated neutrophils. These assays were performed in the following manner.

Adherence of Polymorphonuclear Leukocytes (PMN) to Serum Coated Wells

Isolation of PMN: Blood was drawn into syringes containing heparin (1 U/mL), from human volunteers (free of any medication for at least 48 hrs). 30 mL of blood was layered over a gradient of 10 mL 1.077 g/mL Histpaque (Sigma, St. Louis, Mo.), and centrifuged at room temperature, 400×g for 20 min. All subsequent manipulations were carried out at room temperature, with endotoxin free reagents, and using polypropylene pipettes and tubes, to prevent activation of the PMN. The pinkish PMN layer immediately above the RBC was collected and washed 2× with Hank's buffered salt solution with calcium and magnesium, 0.2% glucose, and 10 mM HEPES, pH 7.2 (HBSS+ +) by centrifugation at 400×g for 10 min. Pellets were suspended in 8 mL 0.9% NaCl, and RBC lysed by the addition of 24 mL water for 40 sec, followed by the addition of 8 mL of 3.6% NaCl. After centrifugation at 200×g for 8 min, RBC ghosts were aspirated from the top of the PMN pellet, and cells washed with HBSS++. PMN adherence to protein substrates: 96 well tissue culture plates were coated with 10% pooled human serum (North American Biological, ,;, Miami, Fla.) in phosphate buffered saline (PBS) for 1 hr at 37° C., followed by washing 3× with PBS. Test compounds were prepared in DMSO as 100× stocks. PMN ($4 \times 10^6$/mL) were preincubated with test compounds for 10 min at 37° C. in serum-coated wells. Tumor necrosis factor (TNF-$\alpha$) was added to 3 nM or platelet aggregation facor (PAF) to 1 $\mu$M, and adherence was carried out for 20 or 10 min, respectively. Nonadherent cells were aspirated, and wells washed two times with warm PBS with calcium and magnesium, with blotting of the inverted plate following each aspiration. Adherent PMN were quantitated using a BCA protein assay (Pierce, Rockford, Ill.).

INF-$\gamma$HUVEC Assay. Primary human umbilical vein endothelial cells (HUVECs) from Clonetics Corp. (San Diego, Calif.) were seeded at 20,000 cells per wall in a 96 well tissue culture plate that was coated with fibronectin, for 45 min and then twice rinsed with phosphate buffered saline. To the culture media (M199, 80%; FBS, 20%; 100 mg/mL endothelial cell growth factor (Maciag et all, *Proc. Natl. Acad. Sci. USA* (1979) 76(11):5674–5678), 0.1 mg/mL heparin; 5% $CO_2$; 37° C.) was added INF-$\gamma$ (R&D Systems) at 1 unit/mL for 20 hrs. Isolated PMNs were loaded with the fluorescent dye BCECF AM (Molecular Probes) by incubating $1 \times 10^7$ cells/mL in HBSS with 4 $\mu$M dye for 30 min at 37° C. The PMNs were incubated with test compound for 10 min at 37° C., then activated with 50 ng/mL TNF and immediately added to the HUVECs which had been rinsed twice with HBSS+1% human serum. The co-culture plate was incubated at 37° C. for 20 min followed by gentle washing (twice) with HBSS+1% human serum. The extent of adherence was assessed by measuring the amount of fluorescence (485–535 nM filter) in each well with a fluorescence plate reader (Idexx).

Superoxide production. Superoxide production by PMN was measured as the superoxide dismutase (SOD)-inhibitable reduction of ferricytochrome c. Preliminary experiments carried out with paired samples containing cytochrome c and cytochrome c plus SOD showed that the reduction of cytochrome c was totally inhibited by SOD. Therefore, subsequent experiments were performed in the presence of cytochrome c only. In all cases, experiments were carried out in 96 well plates. Before the addition of cells, plates were coated by incubating each well with 200 $\mu$l of 10% human serum for 1 h in 37° C. Plates were then washed several times with PBS containing 10 mM $CaCl_2$ and $MgCl_2$. Neutrophils, resuspended in Hank's balanced salt solution (HBSS) to a final concentration of $4 \times 10^6$ cells/ml, were preincubated with TNF (10 ng/ml) for 10 min at 37° C. in the presence of cytochrome c (75 $\mu$m). Experiments were then performed with 100 $\mu$l of this cell suspension added to each well, followed by the addition of 10 $\mu$l of an aqueous dilution of test compound (50 nm–500 gm). Immediately after the addition of test compound, a 10 $\mu$l aliquot of activators (fMLP, 300 nM; PAF, 20 nM; C5a, 5 $\mu$g/ml) was added to each well. Plates were immediately transferred to a preheated Thermomax kinetic microplate reader and the change in absorbance at 500 nM was recorded over a 3 min period. The resulting rates were plotted against test compound concentration and the $IC_{50}$s corresponding to specific test compounds were derived directly from this data.

Elastase release. Neutrophils ($5 \times 10^6$/ml in HBSS) were preincubated for 5 min at 37° C. with cytochalasin b (5 $\mu$g/ml). Experiments were performed in microtubes (96 per rack) to which were added the cell suspension, test compound (50 nM–500 $\mu$M), and one of several activators (fMLP, 200 nM, C5a, 24 nM; PAF, 20nM). After incubation (30 min, 37° C.) the tubes were centrifuged (1 min, 1500 rpm) and the supernatants assayed for elastase activity according to the following protocol:

Specifically, 10 $\mu$l of purified human neutrophil elastase standard or of sample was added to 70 $\mu$l or 0.1M Tris pH 7.5, 0.5% Brij detergent and 10 $\mu$l or 5 mM elastase substrate (methoxysuccinyl-alanyl-alanyl-prolyl-valyl paranitroanilide) in a 96 well microliter plate. Plates were inbudated for 60 min at 37° C. and absorbance was read at 410 nM on a microplate reader. Elastase activity was quantitated relative to standards. The determination were plotted against test compound dose and the $IC_{50}$s corresponding to specific test compounds were derived directly from this data.

The following compounds of the invention were tested in the in vitro assays.

| | |
|---|---|
| NPC 18730 | 4-[2-(biphenyl)-E-ethenyl]benzoic acid |
| NPC 18731 | 4-[2-(biphenyl)ethyl]benzoic acid |
| NPC 18812 | 4-{2-[2-(2-naphthyl)phenyl]-(E)-ethenyl}benzoic acid |
| NPC 18818 | 4-{2-[2-(3,4-dichlorophenyl)phenyl]-(E)-ethenyl]benzoic acid |
| NPC 18801 | 2'-phenoxy-4-stilbenecarboxylic acid |
| NPC 18915 | 4-{2-[2-(2-benzofuranyl)phenyl]-(E)-ethenyl}benzoic acid |

TABLE I

| | $IC_{50}$ ($\mu$M) to inhibit adhesion | | |
|---|---|---|---|
| Cmpd | TNF-$\alpha$ serum | PAF serum | IFN-$\gamma$ HUVECS |
| NPC 18730 | 2.9 | 2.4 | 25.7 |
| NPC 18731 | 6.4 | 6.5 | 28 |
| NPC 18812 | 3.6 | 1.17 | 14.5 |
| NPC 18818 | 1.8 | 0.41 | 30.0 |
| NPC 18801 | 6.9 | 0.86 | 52.4 |
| NPC 18915 | n.t. | 0.64 | n.t. |

TABLE II

| | $IC_{50}$ to inhibit elastase release ($\mu$M) | | $IC_{50}$ to inhibit superoxide production ($\mu$M) | |
|---|---|---|---|---|
| Cmpd | fMLP/ER | PAF/ER | fMLP/$O_2$ | PAF/$O_2$ |
| NPC 18730 | 6.25 | 3.23 | 0.34 | 3.0 |
| NPC 18731 | 8.7 | 19.85 | n.t. | n.t. |
| NPC 18812 | n.t. | 7.6 | n.t. | n.t. |
| NPC 18818 | 1.2 | 0.81 | 0.15 | 0.30 |
| NPC 18801 | 7.5 | 0.6 | 0.15 | 0.52 |

In Vivo Assays

Two in vivo models of inflammation were used to assess the anti-inflammatory activity of compounds of the invention. One model measures neutrophil accumulation in thioglycollate-induced peritonitis in mice. The other measures neutrophil accumulation in the cutaneous Reverse Passive Arthus reaction in rats. These assays were carried out as follows.

Neutrophil Accumulation in Thiogylcollate-induced Peritonitis in the Mouse

Thioglycollate broth has previously been shown to induce acute peritonitis in vivo and the procedure used here was modified from that reported by Watson et al. (Watson, et al. *Nature* (1991) 349:164–167). Male CF-1 mice were pretreated with individual test compound (4–6 mice per compound) 10 min prior to thioglycollate treatment. Test compounds at various doses, solubilized in 1% Tween, pH 9.0, were injected into the tail vein. Thioglycollate (4% Brewer's thioglycollate broth in water) was administered intraperitoneally in 1 ml volume. Peritoneal lavages, performed 4 hrs following thioglycollate treatment, involved injecting 5 ml of Dulbecco's phosphate buffered saline with 0.1% bovine serum albumin and 10 units/ml heparin into the peritoneal cavity, massaging the peritoneum, and then removing fluid through peritoneal aspiration. The lavage fluid was centrifuged, red blood cells lysed with water, cells were resuspended in Hank's balanced salt solution, and leukocytes were counted with a modified Neubauer hemacytometer. Leukocyte preparations (cytospin slides) were differentially stained with a Giemsa stain. Neutrophil accumulation expressed as a percent of control was calculated after the subtraction of baseline neutrophils from all treatement groups (see Table III). All test compounds demonstrated significant inhibition of neutrophil accumulation in the peritoneal cavity at 4 hrs following thioglycollate treatment.

Neutrophil Accumulation in the Cutaneous Reverse Passive Arthus Reaction in Rats Male Sprague Dawley rats were treated with test compounds by intraperitoneal injection of 1.4 mg/kg in 1% Tween, pH 9.0 vehicle. After 1 hr, animals were lightly anesthetized with 2% isoflurane, v/v, injected by intravenous route with 1 ml of 5 mg/ml human serum albumin, immediately follwed by intracutaneous administration of 75 µl of a solution of 4 mg/ml of goat anti-human serum albumin. Animals were anesthetized 4 hrs after antigen-antibody treatment. Punch biopsies of the dorsal injection sites were performed with one biopsy weighed for wet/dry weight ratio determination. The remaining two skin biopsies were used for measuring myeloperoxidase content and were minced, weighed and homogenized for 30 sec in 20 mM phosphate buffer (pH 7.4). After centrifugation (20 min, 6000×g, 4° C.) the supernatant was decanted and the pellet resuspended in 50 mM phosphate buffer (pH 6.0) containing 0.5% hexadecyltrimethylammonium bromide. After three freeze/thaw cycles, the pellet was centrifuged (15 min, 20000×g, 4° C.) and 100 µl aliquots were added to 2.9 ml of assay buffer (50 mM phosphate buffer, 0.167 mg/ml o-dianiside, 0.05% $H_2O_2$, pH 6.0). Absorbance at 460 nM was measured at 15 min. Results shown in Table IV were calculated as absorbance units/g dry weight.

TABLE III

Inhibition of neutrophil accumulation in thiogylcollate-induced peritonitis

| Cmpd | Dose (mg/kg) | % Inhibition | $ED_{50}$ (mg/kg) |
|---|---|---|---|
| 18731 | 3 | 22 | 4 |
|  | 10 | 44 |  |
|  | 30 | 59 |  |
|  | 60 | 59 |  |
| 18812 | 3 | 12 | 7 |
|  | 10 | 50 |  |
|  | 30 | 71 |  |
|  | 60 | 94 |  |
| 18730 | 0.3 | 16 | 0.8 |
|  | 1 | 20 |  |
|  | 3 | 67 |  |
|  | 10 | 37 |  |
|  | 30 | 48 |  |
| 18801 | 3 | 36 | <10 |
|  | 10 | 65 |  |
|  | 30 | 65 |  |
| 18818 | 3 | 35 | <30 |
|  | 10 | 34 |  |
|  | 30 | 52 |  |

TABLE IV

Inhibition of neutrophil accumulation in Reverse Passive Arthus

| Test Compound (1.4 mg/kg) | Reverse Passive Arthus % Inhibition (n = 4) | $ID_{50}$ mg/kg |
|---|---|---|
| 18730 | 40% |  |
| 18731 | 40% | 0.1 |
| 18801 | 3% |  |
| 18812 | 29% | 0.5 |
| 18818 | 8% |  |

We claim:

1. A compound of the formula:

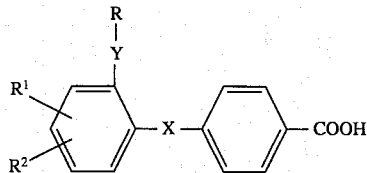

wherein

—X— represents $C_1$ to $C_6$ alkylene, $C_2$ to $C_6$ alkenylene or a divalent moiety having the structure —$(CH_2)$m—Z— in which m is an integer from 0 to 3 and Z represents —O—, —S— or —NH—;

—Y— represents a direct bond, C1 to $C_6$ alkylene, $C_2$ to $C_6$ alkenylene or a divalent moiety having the structure —$(CH_2)_m$—Z—$(CH_2)_n$ in which m and n are each, independently, an integer from 0 to 3 and —Z— represents —O—, —S— or —NH—;

R represents a 5- or 6-membered carbocyclic or heterocyclic ring or a carbocyclic or heterocyclic: fused ring system containing up to 10 members in the ring, which carbocyclic, heterocyclic: or fused ring system may be saturated or unsaturated and may contain up to two substituents selected from lower alkyl, methoxy, halo and trifluoromethyl; and $R^1$ and $R^2$ are each, independently selected from hydrogen, lower alkyl, methoxy, halo and trifiuoromethyl, or a pharmaceutically acceptable salt thereof.

2. A compound of claim 1 wherein —X— is selected from $C_1$ to $C_6$ alklylene and $C_2$ to $C_6$ alkenylene.

3. A compound of claim 1 wherein —X— is selected from ethylene and ethenylene.

4. A compound of claim 1 wherein —Y— is selected from a direct bond, —O—, —S—, —NH— and —CH$_2$O—.

5. A compound of claim 1 wherein —Y— is a direct bond.

6. A compound of claim 1 wherein $R^1$ and $R^2$ are both hydrogen.

7. A compound of claim 1 wherein R is phenyl, which may be mono- or di-substituted at the meta and/or para positions with chloro, methyl or trifluoromethyl; or naphthyl.

8. A compound selected from the group consisting of:
4-[2-(2-biphenyl)-E-ethenyl]benzoic acid;
4-[2-(2-biphenyl)ethyl]benzoic acid;
4-{2-[2-(2-naphthyl)phenyl]-(E)-ethenyl}benzoic acid;
4-{2-[2-(3,4-dichlorophenyl)phenyl]-(E)-ethenyl}benzoic acid; and
2'-phenoxy-4-stilbenecarboxylic acid.

9. A pharmaceutical composition for treating an inflammatory condition comprising an anti-inflammatory amount of a compound of the formula:

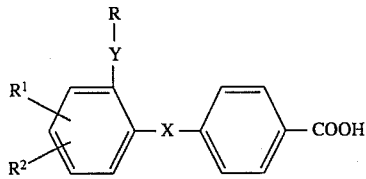

wherein
—X— represents $C_1$ to $C_6$ alkylene, $C_2$ to $C_6$ alkenylene or a divalent moiety having the structure —(CH$_2$)$_m$—Z— in which m is an integer from 0 to 3 and Z represents —O—, —S—, or —NH—;

—Y— represents a direct bond, $C_1$ to $C_6$ alkylene, $C_2$ to $C_6$ alkenylene or a divalent moiety having the structure —(CH$_2$)$_m$—Z—(CH$_2$)$_n$— in which m and n are each, independently, an integer from 0 to 3 and Z represents —O—, —S— or —NH—;

R represents a 5- or 6-membered carbocyclic or heterocyclic ring or a carbocyclic or heterocyclic fused ring system containin up to 10 members in the ring, which carbocyclic, heterocyclic or fused ring system may be saturated or unsaturated and may contain up to two substituents selected from lower alkyl, methoxy, halo and trifluoromethyl; and $R^1$ and $R^2$ are each independently, selected from hydrogen, lower alkyl, methoxy, halo and trifluoromethyl, or a pharmaceutically acceptable salt thereof; and a pharmaceutically acceptable carrier vehicle.

10. A composition of claim 9 wherein —X— is selected from $C_1$ to $C_6$ alkylene and $C_2$ to $C_6$ alkenylene.

11. A composition of claim 9 wherein —X— is selected from ethylene and ethenylene.

12. A composition of claim 9 wherein —Y is selected from a direct bond, methylene, —O— and —CH$_2$O—.

13. A composition of claim 9 wherein —Y— is a direct bond.

14. A composition of claim 9 wherein R is phenyl, which may be mono- or di-substituted at the meta and/or para positions with chloro, methyl or trifluoromethyl, or naphthyl.

15. A composition of claim 9 wherein $R^1$ and $R^2$ are both hydrogen.

16. A composition of claim 9 wherein the compound of Formula I is selected from the group consisting of
4-[2-(2-biphenyl)-E-ethenyl]benzoic acid;
4-[2-(2-biphenyl)ethyl]benzoic acid;
4-{2-[2-(2-naphthyl)phenyl]-(E)-ethenyl}benzoic acid;
4-{2-[2-(3,4-dichlorophenyl)phenyl]-(E)-ethenyl}benzoic acid; and
2'-phenoxystilbenecarboxylic acid.

17. A method of treating a subject suffering from an inflammatory condition which comprises administering to such subject an anti-inflammatory amount of a compound of the formula:

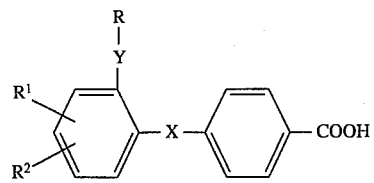

wherein
—X— represents $C_1$ to $C_6$ alkylene, $C_2$ to $C_6$ alkenylene or a divalent moiety having the structure —(CH$_2$)$_m$—Z— in which m is an integer from 0 to 3 and Z represents —O—, —S— or —NH—;

—Y— represents a direct bond, $C_1$ to $C_6$ alkylene, $C_2$ to $C_6$ alkenylene or a divalent moiety having the structure —(CH$_2$)$_m$—Z—(CH$_2$)$_n$— in which m and n are each, independently, an integer from 0 to 3 and Z represents —O—, —S— or —NH—;

R represents a 5- or 6-membered carbocyclic or heterocyclic ring or a carbocyclic or heterocyclic fused ring system containing up to 10 members in the ring, which carbocyclic, heterocycclic or fused ring system may be saturated or unsaturated and may contain up to two substituents selected from lower alkyl, methoxy, halo and trifluoromethyl; and $R_1$ and $R^2$ are each, independently, selected from hydrogen, lower alkyl, methoxy, halo and trifluoromethyl, or a pharmaceutically acceptable salt thereof.

18. The method of claim 17 wherein —X— is selcted from $C_1$ to $C_6$ alkylene and $C_2$ to $C_6$ alkenylene.

19. The method of claim 17 wherein —X— is selected from ethylene and ethenylene.

20. The method of claim 17 wherein —Y— is selected from a direct bond, —O—, —S—, —NH— and —CH$_2$O—.

21. The method of claim 17 wherein —Y— is a direct bond.

22. The method of claim 17 wherein R is phenyl, which may be mono- or di-substituted at the meta and/or para positions with chloro, methyl or trifluoromethyl.

23. The method of claim 17 wherein $R^1$ and $R^2$ are both hydrogen.

24. The method of claim 17 wherein the compound of Formula I is selected from the group consisting of:
4-[2-(2-biphenyl)-E-ethenyl]benzoic acid;
4-[2-(2-biphenyl)ethyl]benzoic acid;
4-{2-[2-(2-naphthyl)phenyl]-(E)-ethenyl}benzoic acid;
4-{2-[2-(3,4-dichlorophenyl)phenyl]-(E)-ethenyl}benzoic acid;
2'-phenoxystilbenecarboxylic acid,
and pharmaceutically acceptable salts thereof.

* * * * *

UNITED STATES PATENT AND TRADEMARK OFFICE
CERTIFICATE OF CORRECTION

PATENT NO. : 5,530,157
DATED : June 25, 1996
INVENTOR(S) : Richard Mewshaw and Gregory S. Hamilton It is certified that error appears in the above-identified patent and that said Letters Patent is hereby corrected as shown below:

In claim 16, column 26, line 8, please delete "2'-phenoxystilbenecarboxylic acid" and insert therefor --2'-phenoxy-4-stilbenecarboxylic acid--.

In claim 24, column 26, line 64, please delete "2'-phenoxystilbenecarboxylic acid" and insert therefor --2'-phenoxy-4-stilbenecarboxylic acid--.

Signed and Sealed this

Sixth Day of January, 1998

*Attest:*

BRUCE LEHMAN

*Attesting Officer*     Commissioner of Patents and Trademarks